(12) United States Patent
Bartosz et al.

(10) Patent No.: US 10,725,007 B2
(45) Date of Patent: Jul. 28, 2020

(54) AIRCRAFT COCKPIT PORTABLE COMPONENT GAS SENSOR

(71) Applicant: Hamilton Sundstrand Corporation, Charlotte, NC (US)

(72) Inventors: Lance R. Bartosz, Granby, MA (US); Joseph V. Mantese, Ellington, CT (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 216 days.

(21) Appl. No.: 15/847,141

(22) Filed: Dec. 19, 2017

(65) Prior Publication Data
US 2019/0187115 A1 Jun. 20, 2019

(51) Int. Cl.
| | |
|---|---|
| *G01N 33/00* | (2006.01) |
| *B64D 13/00* | (2006.01) |
| *G08B 21/14* | (2006.01) |
| *B64D 43/00* | (2006.01) |
| *B64D 45/00* | (2006.01) |
| *G08B 25/08* | (2006.01) |

(52) U.S. Cl.
CPC ......... *G01N 33/0063* (2013.01); *B64D 13/00* (2013.01); *B64D 43/00* (2013.01); *B64D 45/00* (2013.01); *G01N 33/004* (2013.01); *G01N 33/0049* (2013.01); *G08B 21/14* (2013.01); *G08B 25/08* (2013.01); *B64D 2045/0075* (2013.01)

(58) Field of Classification Search
CPC ........... G01N 33/0063; G01N 33/0049; G01N 33/004; G08B 25/08; G08B 21/14; B64D 2045/0075; B64D 13/00; B64D 43/00; B64D 45/00
See application file for complete search history.

(56) References Cited

U.S. PATENT DOCUMENTS

| | | | |
|---|---|---|---|
| 6,452,510 B1 | 9/2002 | Zysko | |
| 7,746,240 B2 * | 6/2010 | Vij | G08B 21/14 340/540 |
| 8,289,172 B2 | 10/2012 | Matos | |

(Continued)

FOREIGN PATENT DOCUMENTS

| | | |
|---|---|---|
| EP | 2706423 A2 | 3/2014 |
| EP | 3210891 A1 | 8/2017 |
| WO | WO 2017070815 A1 | 5/2017 |

OTHER PUBLICATIONS

Extended European Search Report for European Patent Application No. 18214125.9 dated Apr. 24, 2019, 8 pages.

*Primary Examiner* — Randy W Gibson
*Assistant Examiner* — Gedeon M Kidanu
(74) *Attorney, Agent, or Firm* — Kinney & Lange, P.A.

(57) ABSTRACT

A system includes a portable air sensing device and an electronic interface device. The portable air sensing device is configured to sense a concentration of component gas in surrounding air and wirelessly transmit the sensed concentration. The electronic interface device is positioned within a cockpit of an aircraft and is communicatively coupled with the portable air sensing device. The electronic interface device is configured to receive the wirelessly transmitted concentration from the portable air sensing device, and generate, for display, an indication of the received concentration in relation to a defined threshold maximum concentration of the component gas.

16 Claims, 5 Drawing Sheets

(56) References Cited

U.S. PATENT DOCUMENTS

| | | | |
|---|---|---|---|
| 2006/0111793 A1* | 5/2006 | Stokes | G05B 15/02 |
| | | | 700/3 |
| 2010/0294885 A1* | 11/2010 | Bloch | A62B 25/005 |
| | | | 244/118.5 |
| 2013/0338857 A1 | 12/2013 | Sampigethaya | |
| 2014/0074322 A1* | 3/2014 | Baumgarten | G05B 23/0216 |
| | | | 701/3 |
| 2016/0212618 A1* | 7/2016 | Henzl | H04B 5/0025 |
| 2016/0355262 A1 | 12/2016 | Sharma | |
| 2017/0069136 A1* | 3/2017 | Sharma | G02B 27/017 |
| 2017/0168566 A1 | 6/2017 | Osterhout et al. | |
| 2018/0301013 A1* | 10/2018 | Wang | G01N 33/0075 |

* cited by examiner

AIRCRAFT COCKPIT PORTABLE COMPONENT GAS SENSOR

BACKGROUND

The present disclosure relates generally to air sensing devices, and in particular to portable air sensing devices for sensing concentrations of a component gas in aircraft cockpits.

Commercial aircraft typically incorporate an environmental control system (ECS) that provides a conditioned supply of air for thermal control and cabin pressurization of the aircraft. The ECS is often turned off, however, during passenger boarding when the aircraft is disconnected from airport utilities and prior to engine startup. The supply of air to the cockpit or other portions of the aircraft is therefore unconditioned and often uncirculated during passenger boarding or at other times when the ECS is inactive, thereby possibly resulting in an increased concentration of certain component gases of the cockpit air. For instance, it has been shown that cockpit carbon dioxide ($CO_2$) levels (i.e., concentration of $CO_2$ in the air) can rise significantly when the ECS is turned off. Such increases in $CO_2$ can be exacerbated during times of passenger boarding, thereby resulting in significant increases in $CO_2$ concentrations. Increased concentrations of $CO_2$ and other gases, such as carbon monoxide (CO), have been shown to negatively impact human cognitive abilities. Accordingly, an increased concentration of such component gases arising, e.g., during passenger boarding, can potentially impact the cognitive abilities of pilots during challenging maneuvers, such as an engine fault during aircraft takeoff.

SUMMARY

In one example, a system includes a portable air sensing device and an electronic interface device. The portable air sensing device is configured to sense a concentration of a component gas in surrounding air and wirelessly transmit the sensed concentration. The electronic interface device is positioned within a cockpit of an aircraft and is communicatively coupled with the portable air sensing device. The electronic interface device is configured to receive the wirelessly transmitted concentration from the portable air sensing device, and generate, for display, an indication of the received concentration in relation to a defined threshold maximum concentration of the component gas.

In another example, a system includes a portable air sensing device, an electronic interface device, and a portable computing device having a display. The portable air sensing device is configured to sense a concentration of a component gas in surrounding air and wirelessly transmit the sensed concentration and time data identifying a time when the concentration of the component gas was sensed. The electronic interface device is positioned within a cockpit of an aircraft and is communicatively coupled with the portable air sensing device. The electronic interface device is configured to receive the wirelessly transmitted concentration of the component gas and time data from the portable air sensing device, and generate, for display, an indication of the received concentration of the component gas in relation to the time data. The portable computing device is communicatively coupled to the electronic interface device and is configured to display the indication of the received concentration of the component gas in relation to the time data.

In another example, a method includes sensing, by a gas sensor of a portable air sensing device, concentration of a component gas in surrounding air, and wirelessly transmitting, by the portable air sensing device, the sensed concentration of the component gas. The method further includes receiving, by an electronic interface device positioned within a cockpit of an aircraft, the sensed concentration of the component gas wirelessly transmitted by the portable air sensing device, and generating, by the electronic interface device, an indication of the received concentration of the component gas for display in relation to a defined threshold maximum concentration of the component gas.

DETAILED DESCRIPTION

As described herein, a portable air sensing device measures concentration of a component gas of cockpit air and wirelessly transmits the concentration data to a tablet interface module of an Electronic Flight Bag (EFB) system for display, trend plotting, and alert generation when concentration levels of the component gas are elevated. As such, a system implementing techniques of this disclosure can alert pilots or other flight crew of elevated component gas concentrations to enable remedial action, such as activation of an aircraft Environmental Control System (ECS), to help prevent exposure to excessive levels of, e.g., carbon dioxide ($CO_2$), carbon monoxide (CO), tricresyl phosphate (TCP), volatile organic compounds (VOCs), ozone ($O_3$), or other component gases that can diminish cognitive abilities or otherwise affect human health. The air sensing device described herein is portable in nature (e.g., small in size to enable the device to be carried within flight crew luggage), is self-powered via an internal battery, and communicates wirelessly to a Tablet Interface Module (TIM) or other electronic interface of the EFB system. As such, the portable air sensing device implementing techniques of this disclosure can be utilized in an aircraft cockpit (e.g., in combination with an aircraft EFB system) without the incorporation of additional sensors or equipment within the cockpit itself, thereby increasing usability and ease of integration with existing aircraft platforms.

While the examples of FIGS. 1-5 are described herein within the context of a $CO_2$ sensor that measures $CO_2$ concentrations within the surrounding air, aspects of this disclosure are not so limited. That is, it should be understood that the techniques described herein are applicable to component gases other than $CO_2$, such as CO, TCP, VOCs, $O_3$, or other component gases.

Figure 1:
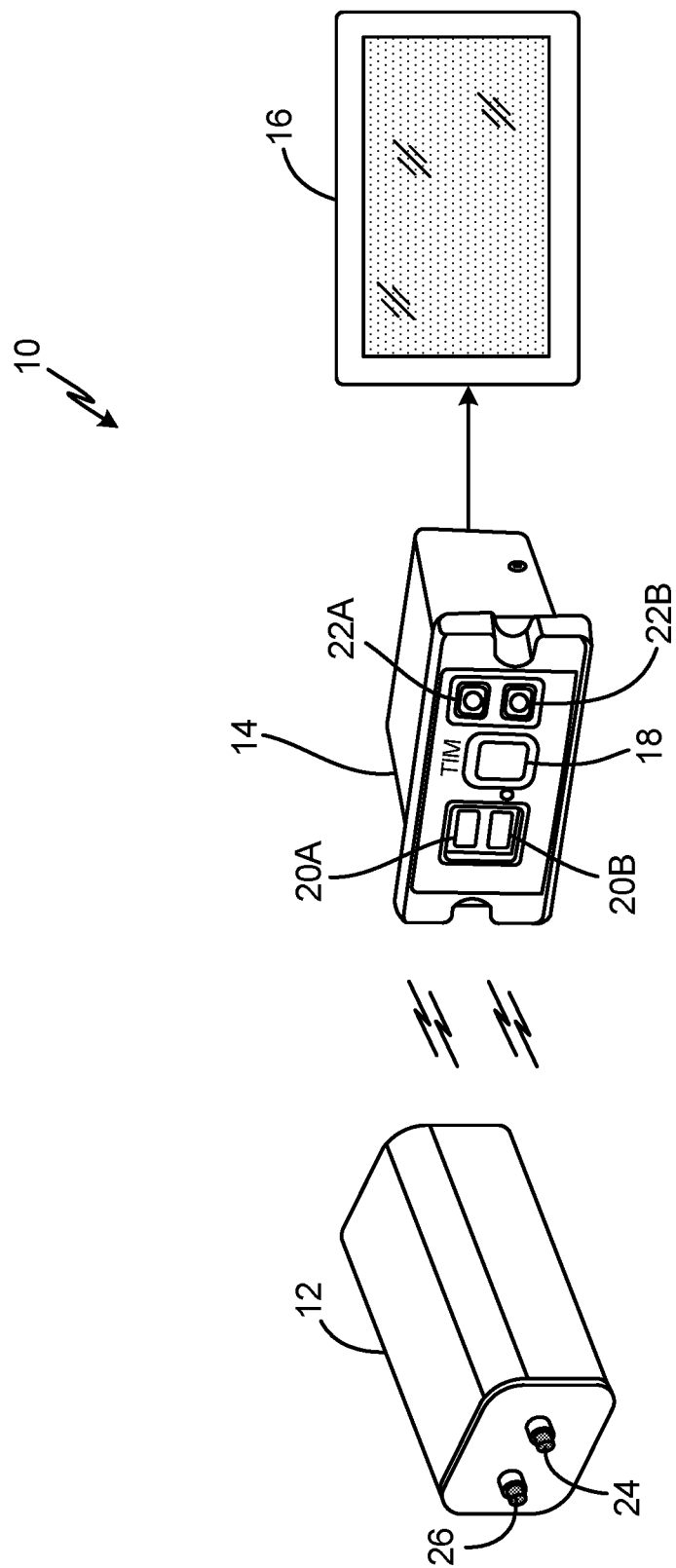
FIG. 1 is a schematic diagram of one example of an aircraft electronic flight bag (EFB) system including a portable air sensing device configured to sense carbon dioxide concentrations.

FIG. 1 is a schematic diagram of aircraft electronic flight bag (EFB) system 10 including portable air sensing device 12 configured to sense carbon dioxide concentrations within the surrounding air. As illustrated in FIG. 1, EFB system 10 further includes Tablet Interface Module (TIM) 14 and display device 16. EFB system 10 is an electronic information management system of the aircraft that stores and displays (e.g., at display device 16) traditional paper-based materials, such as aircraft operating manual information, flight crew operating manual information, navigational charts, and other information, to increase the ease and efficiency of access to such information. EFB system 10, in the example of FIG. 1, is a simplified EFB system including a single TIM and a single display device. In other examples, such as the example of FIG. 2, EFB system 10 can include multiple air sensing devices, TIMs, and display devices, as well as other components that function collectively to provide EFB capabilities to reduce pilot workload and increase ease and efficiency of the display of information within the cockpit.

TIM 14 is an electronic interface device located within the cockpit of the aircraft. TIM 14 manages operation of EFB system 10 and enables user (e.g., pilot) interaction to display selected information at display device 16. In addition, TIM 14 can coordinate the transfer of data between various aircraft components and/or systems and EFB system 10, as is further described below. TIM 14, as illustrated in the example of FIG. 1, includes power button 18, interface ports 20A and 20B, and wireless communication synchronization buttons 22A and 22B. Actuation of power button 18 alternately turns TIM 14 (and effectively EFB system 10) on and off. That is, in response to user actuation of power button 18, TIM 14 alternates between an ON state during which TIM 14 draws electrical current from, e.g., an electrical power bus of the aircraft for operation of components of TIM 14 and an OFF state during which TIM 14 does not draw electrical current from the electrical power bus of the aircraft for operation.

Interface ports 20A and 20B, in the example of FIG. 1, are Universal Serial Bus (USB) ports via which TIM 14 sends and receives data with various external devices, such as display device 16 or other external devices. Though illustrated in FIG. 1 as USB ports, in other examples, interface ports 20A and 20B can be other types of interface ports, such as serial ports, Ethernet ports, or other types of interface ports. Actuation of wireless communication synchronization buttons 22A and 22B enables user (e.g., pilot) interaction to initialize (e.g., synchronize) wireless communication connections between TIM 14 and one or more electronic devices, such as display device 16, portable air sensing device 12, or other electronic devices. That is, in the example of FIG. 1, TIM 14 includes wireless communications devices, such as Bluetooth transceivers, 3G, 4G, LTE, and/or WiFi radio transceivers, or other types of wireless communication devices that enable wireless communication with external devices. In the example of FIG. 1, TIM 14 includes two Bluetooth transceivers, and wireless communication synchronization buttons 22A and 22B are Bluetooth synchronization buttons that initiate pairing of the Bluetooth transceivers with a corresponding Bluetooth transceiver from an external device, such as display device 16 and/or portable air sensing device 12.

TIM 14 is configured to be installed within the cockpit of an aircraft and includes electrical power and communication ports (not illustrated) for connection to an aircraft electrical power bus and one or more aircraft data buses. Display device 16, in the example of FIG. 1, is a tablet computer that can be removed from the aircraft cockpit and carried with the pilot or other flight crew for use with, e.g., different aircraft flights or other uses. That is, in the example of FIG. 1, display device 16 is a tablet computer having an integrated display screen (e.g., a touch-sensitive display), though in other examples, display device 16 can take the form of other portable display devices (e.g., smartphones, laptop computers, or other portable devices having an integrated display). In some examples, display device 16 can be a display screen that is integrated with the cockpit electronics, such as a dedicated EFB display mounted in the cockpit, a display screen of an Electronic Flight Instrument System (EFIS) of the cockpit, or other display screen of the cockpit electronics.

Air sensing device 12 is portable in nature, meaning that air sensing device 12 is physically sized to accommodate transportation of air sensing device 12 between aircraft and between flights, such as within a pocket of a flight bag of the pilot. For instance, in one example, portable air sensing device 12 has a length of 5 inches, a width of 3.5 inches, and a thickness of 2.25 inches, though other physical dimensions are possible. As illustrated in FIG. 1, portable air sensing device 12 includes power button 24 and wireless communications synchronization button 26. In addition, as is further described below, portable air sensing device 12 includes processing circuitry, computer-readable memory, one or more communication devices, and a carbon dioxide ($CO_2$) sensor that all are enclosed within the outer housing of portable air sensing device 12 and not illustrated in the example of FIG. 1. In some examples, air sensing device 12 includes additional sensors, such as a temperature sensor, a pressure sensor, a humidity sensor, or other types of sensors for transmission of corresponding data to TIM 14 during operation. Similarly, in some examples, air sensing device 12 can alternatively and/or additionally include sensors configured to sense component gases other than $CO_2$, such as any one or more of CO, TCP, VOCs, $O_3$, or other component gases.

Actuation of power button 24 transitions portable air sensing device 12 between an OFF state (or hibernation state) during which air sensing device 12 does not draw power from an internal battery for operation of sensors and other electrical components, and an ON state during which air sensing device 12 senses $CO_2$ concentrations in the surrounding air via the $CO_2$ sensor and wirelessly transmits the $CO_2$ concentration data. Actuation of wireless communications synchronization button 26 causes portable air sensing device 12 to synchronize communications with a nearby or selected electronic device, such as TIM 14. For example, wireless communications synchronization button 26 can be a Bluetooth pairing button that initiates the pairing of portable air sensing device 12 with TIM 14 via the Bluetooth wireless communication protocol.

As illustrated in FIG. 1, portable air sensing device 12 is communicatively coupled with TIM 14 for wireless communications, such as wireless Bluetooth communications, WiFi communications, cellular communications, or other wireless communications. In other examples, portable air sensing device 12 can include one or more communications ports that enable wired communications between portable data sensing device 12 and TIM 14, such as an Ethernet port, a USB connector (e.g., male or female connector), a serial communications data port, or other communications data port for wired communications. TIM 14 is communicatively coupled with display device 16 for wireless and/or wired communications. For instance, TIM 14 can communicate wirelessly with display device 16 via Bluetooth, WiFi, cellular, or other wireless communications. In some examples, TIM 14 can communicate with display device 16 via wired communications, such as via interface port 20A and/or interface port 20B.

In operation, a pilot, copilot, or other flight crew initiates operation of EFB system 10 via actuation of power button 18. In addition, power button 24 of portable air sensing device 12 is actuated to initiate operation of portable air sensing device 12. Actuation of one of wireless communication synchronization buttons 22A and 22B as well as wireless communications synchronization button 26 initiates the synchronization of wireless communications between portable air sensing device 12 and TIM 14, such as via Bluetooth communications. Display device 16 is communicatively coupled with TIM 14, such as via Bluetooth pairing or other wireless communications, wired communications (e.g., USB, Ethernet, or other wired communications), or both.

Portable air sensing device 12 senses a concentration of $CO_2$ in the surrounding air via the $CO_2$ sensor and wirelessly transmits the $CO_2$ concentration data to TIM 14. In some examples, such as when the portable air sensing device 12 includes additional sensors, such as one or more of a temperature sensor, a pressure sensor, a humidity sensor, or other additional sensors (e.g., sensors configured to sense concentration of one or more of CO, TCP, VOCs, $O_3$, or other component gases), portable air sensing device 12 can transmit the sensed data from the additional sensors to TIM 14. Portable air sensing device 12 senses the concentration of $CO_2$ in the surrounding air and periodically transmits the $CO_2$ concentration data, such as once per second, once per five seconds, or at other sensing and/or transmission periods (regular or irregular). In certain examples, portable air sensing device 12 transmits time data in addition to the $CO_2$ concentration data, the time data identifying when a corresponding $CO_2$ concentration was sensed. For instance, portable air sensing device 12 can transmit the $CO_2$ concentration data as packets of information (e.g., Internet Protocol packets), each packet including time (and, in certain examples, date) information identifying a time when the corresponding $CO_2$ concentration was sensed by the $CO_2$ sensor.

TIM 14 receives the $CO_2$ concentration data from portable air sensing device 12 via the wireless data transmissions, and generates an indication of the received $CO_2$ concentration data for display. For example, TIM 14 can generate (e.g., serve) a web page including the received $CO_2$ concentration data, the web page accessed by display device 16 (e.g., a tablet computer) via Hypertext Transfer Protocol (HTTP) communications using a web browser application executed by display device 16. The web page generated by TIM 14 and accessed by display device 16 includes a graphical representation of the received $CO_2$ concentration data. In examples where portable air sensing device 12 includes sensors configured to sense concentration of one or more of CO, TCP, VOCs, $O_3$, or other component gases, the web page or other display information generated by TIM 14 can include a graphical representation of the corresponding one of the CO, TCP, VOCs, $O_3$, or other component gas. In some examples, TIM 14 can generate the display of the $CO_2$ concentration data as a time series of $CO_2$ concentrations received from portable air sensing device 12. As such, a pilot, copilot, or other flight crew can access the web page via display device 16 to view a trend of the sensed $CO_2$ over time, thereby providing information regarding how the sensed $CO_2$ concentration is changing (e.g., increasing and/or decreasing) with respect to time.

In certain examples, TIM 14 can generate an alert based on a comparison of the received $CO_2$ concentrations to one or more defined threshold maximum $CO_2$ concentrations. For instance, TIM 14 can compare each $CO_2$ concentration received from portable air sensing device 12 to one or more defined maximum threshold concentrations, and can generate the alert in response to determining that the received $CO_2$ concentration meets or exceeds the defined maximum threshold concentration. In other examples, TIM 14 can compare a moving average of received $CO_2$ concentrations (e.g., a moving average of a most recent time duration of $CO_2$ concentrations, such as a time duration of one minute, five minutes, or other time durations), a weighted moving average of the received $CO_2$ concentrations, or other moving averages of the received $CO_2$ concentrations with the one or more defined maximum threshold concentrations.

In some examples, TIM 14 compares the received $CO_2$ concentration data to increasing defined maximum threshold concentrations to generate one of a plurality of alert severity levels. For instance, TIM 14 can compare the received $CO_2$ concentration data to a first defined maximum threshold concentration to generate a first alert (or first severity level of alert) in response to determining that the received $CO_2$ concentration is greater than (or equal to) the first defined maximum threshold concentration, and can compare the received $CO_2$ concentration data to a second defined maximum threshold concentration (greater than the first maximum defined threshold concentration) to generate a second alert (or second, increased severity level of alert) in response to determining that the received $CO_2$ concentration is greater than (or equal to) the second defined maximum threshold concentration.

The first defined maximum threshold concentration can correspond to a first level of $CO_2$ concentration associated with the beginning of impairment of human cognitive abilities, such as 1500 parts per million (ppm) of $CO_2$, 2000 ppm of $CO_2$, or other concentration of $CO_2$ in the surrounding air. The second defined maximum threshold concentration can correspond to a second level of $CO_2$ concentration associated with levels of $CO_2$ concentration that exceed regulatory limits, such as 5000 ppm of $CO_2$ or other concentration of $CO_2$ in the surrounding air. Either or both of the first and second defined maximum threshold concentrations can be configurable, such as via a user interface generated by TIM 14 and accessed via, e.g., display device 16. In addition, TIM 14 can utilize, in some examples, more than two defined maximum threshold concentrations, thereby enabling the generation of more than two types and/or severity levels of alerts. Similarly, in certain examples, TIM 14 can utilize a single defined maximum threshold concentration for the generation of alerts.

TIM 14, in some examples, generates the indication of the received $CO_2$ concentration data for display in relation to the one or more defined maximum threshold concentrations, as is further described below. For instance, TIM 14 can generate data that displays a graph of both the received $CO_2$ concentration with respect to time and one or more lines or other indications corresponding to the one or more defined maximum threshold concentrations. In certain examples, TIM 14 generates a suggested remedial action associated with the alert, such as a suggested remedial action to active an Environmental Control System (ECS) of the aircraft.

Accordingly, portable air sensing device 12 wirelessly transmits $CO_2$ concentrations of air within the cockpit of an aircraft to TIM 14 of EFB system 10 for display, trend plotting and analysis, and alert generation when $CO_2$ concentrations levels are elevated. As such, EFB system 10 implementing techniques of this disclosure can alert pilots, copilots, or other flight crew of elevated $CO_2$ concentrations to enable remedial action, such as activation of an aircraft ECS to reduce the $CO_2$ concentration of the air within the cockpit. Techniques described herein can increase awareness of the $CO_2$ concentration within the aircraft cockpit, thereby enabling the flight crew to take action to decrease the $CO_2$ concentration and avoid possible cognitive impairment that can result from elevated $CO_2$ concentration levels. The portable, self-powered (via battery) air sensing device 12 that communicates wirelessly with TIM 14 enables integration of air sensing device 12 with existing aircraft platforms without the need for additional sensors or equipment within the integrated cockpit electronics, thereby increasing usability and ease of integration of portable air sensing device 12 to provide $CO_2$ concentration data for display to the flight crew.

Figure 2:
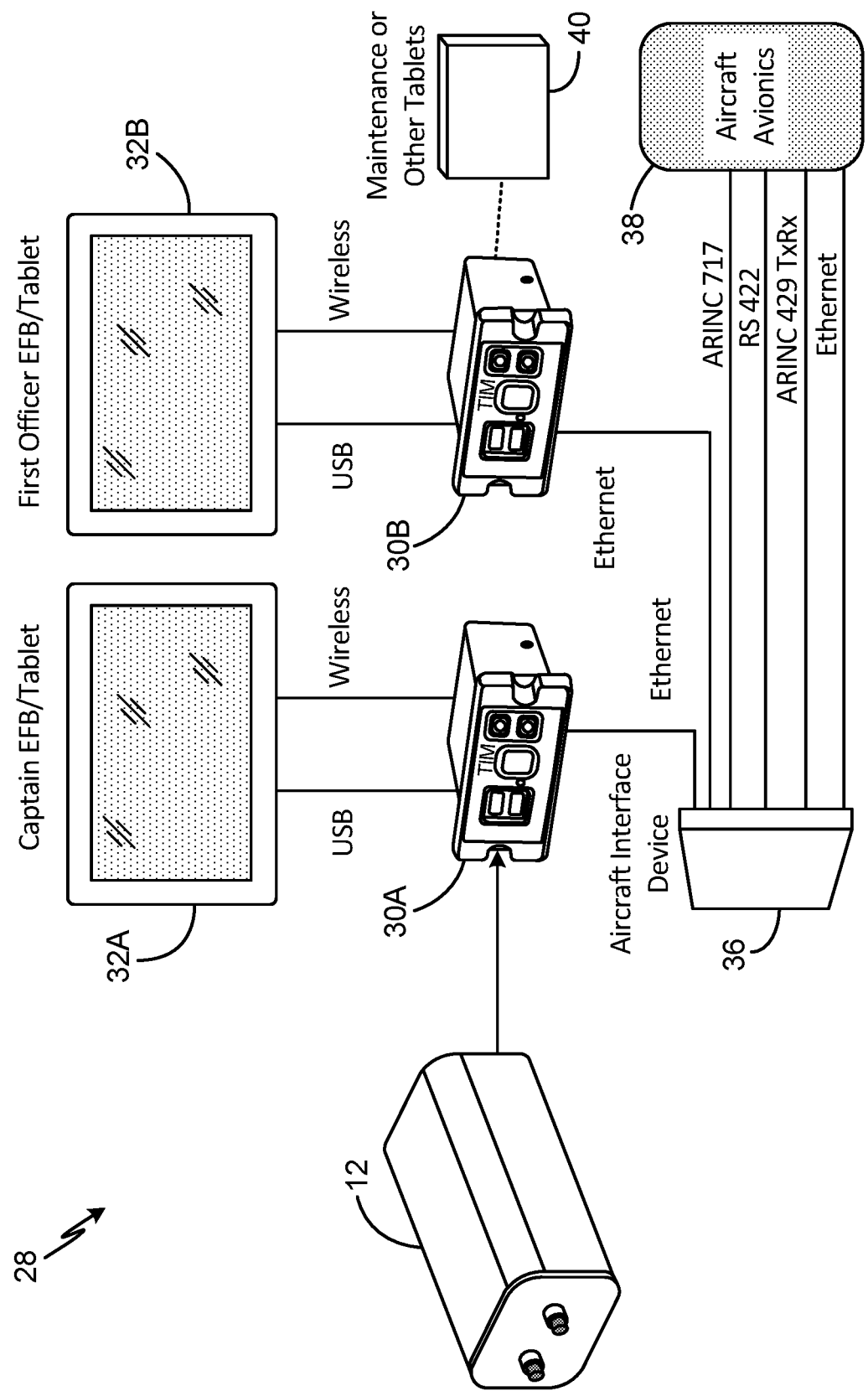
FIG. 2 is a schematic diagram of another example of an aircraft EFB system including the portable air sensing device and multiple interface devices and displays.

FIG. 2 is a schematic diagram of aircraft EFB system 28 including portable air sensing device 12 and multiple interface devices and displays. EFB system 28, illustrated in the example of FIG. 2, is substantially similar to EFB system 10 (FIG. 1), but illustrates the incorporation of multiple interface devices and displays.

As illustrated in FIG. 2, EFB system 28 includes portable air sensing device 12, TIM 30A, TIM 30B, captain display device 32A, first officer display device 32B, aircraft interface device (AID) 36, aircraft avionics inputs 38, and maintenance interface device 40. Each of TIM 30A and TIM 30B are substantially similar to TIM 12 (FIG. 1). Similarly, each of captain display device 32A and first officer display device 32B are substantially similar to display device 16 (FIG. 1). As illustrated in FIG. 2, TIM 30 is communicatively coupled to receive wireless communications from portable air sensing device 12, including sensed $CO_2$ concentration data, time data, and/or other data wirelessly transmitted by portable air sensing device 12. TIM 30B is communicatively coupled with maintenance interface device 40, which can be a portable device (e.g., a tablet computer or other portable electronic device) configured to upload data to EFB system 28 and/or download data from EFB system 28 via the communicative connection with TIM 30B.

As illustrated in FIG. 2, TIM 30A and TIM 30B are both communicatively connected (e.g., via Ethernet or other wired or wireless communication protocols) to send and receive data with AID 36. AID 36 receives inputs from aircraft avionics devices (illustrated as aircraft avionics 38) via one or more aircraft data buses, such as an Aeronautical Radio, Incorporated (ARINC) 717 data bus, an ARINC 429 data bus, an RS 422 data bus, an Ethernet data bus, or other aircraft data buses. Aircraft avionic devices can include, among others, flight management systems, automatic flight control systems, flight control systems, or other aircraft avionic systems and/or corresponding devices. Though illustrated as receiving inputs from aircraft avionics devices 38, it should be understood that AID 36 can receive inputs from any one or more additional aircraft devices and/or systems, such as aircraft ECS systems, aircraft electrical control systems, or other aircraft systems. In some examples, AID 36 receives inputs from one or more aircraft Data Concentrator Units (DCUs) that aggregate information from various aircraft systems and transmit the aggregated data via the one or more aircraft data buses.

In addition, while illustrated as including a single air sensing device 12, in some examples, EFB system 28 can utilize multiple portable air sensing devices. For instance, EFB system 28 can include a first portable air sensing device (e.g., portable air sensing device 12) communicatively connected with TIM 30A and a second portable air sensing device (not illustrated) that is communicatively connected with TIM 30B.

In operation, portable air sensing device 12 transmits $CO_2$ concentration data, time data, and/or other sensed data via wireless communications to TIM 30A. TIM 30A generates an indication of the received $CO_2$ concentration data and generates one or more alerts in response to determining that the received $CO_2$ concentration data is greater than (or equal to) one or more defined maximum threshold $CO_2$ concentration levels. Captain display device 32A accesses the generated display data via wired and/or wireless communications with TIM 30A. In some examples, first officer display device 32B can access the generated display data via wired and/or wireless communications with TIM 30B, which accesses the display data via the communicative connection between AID 36 and TIM 30A. As such, data and/or alerts generated by TIM 30A are accessible by TIM 30B via the communicative connection to AID 36. Similarly, data and/or alerts generated by TIM 30B are accessible by TIM 30A via the communicative connection to AID 36.

In examples where EFB system 28 includes multiple portable air sensing devices (e.g., a first portable air sensing device communicatively connected to TIM 30A and a second portable air sensing device communicatively connected to TIM 30B), data from either or both of the multiple air sensing devices can be accessed via the shared communicative connection between TIM 30A and TIM 30B via AID 36. Similarly, TIM 30A and/or TIM 30B can transmit data to and/or receive data from any one or more aircraft systems (e.g., aircraft avionics 38) via the connection with AID 36. Such $CO_2$ concentration data transmitted by one or more of TIM 30A and TIM 30B can be utilized by receiving systems for alert generation and/or automatic actuation of, e.g., an aircraft ECS in response to a generated alert indicating an elevated $CO_2$ concentration sensed by portable air sensing device 12.

Accordingly, EFB system 28 implementing techniques of this disclosure enables the sensing and display of $CO_2$ concentrations in the aircraft cockpit at any one or more of captain display device 32A and first officer display device 32B. In addition, EFB system 28 can enable such sensed $CO_2$ concentration data to be transmitted to any one or more aircraft systems via the communicative connection with AID 36, thereby disseminating the $CO_2$ information to any one or aircraft systems, such as aircraft ECS system, for alerts and/or automatic activation of the system.

Figure 3:
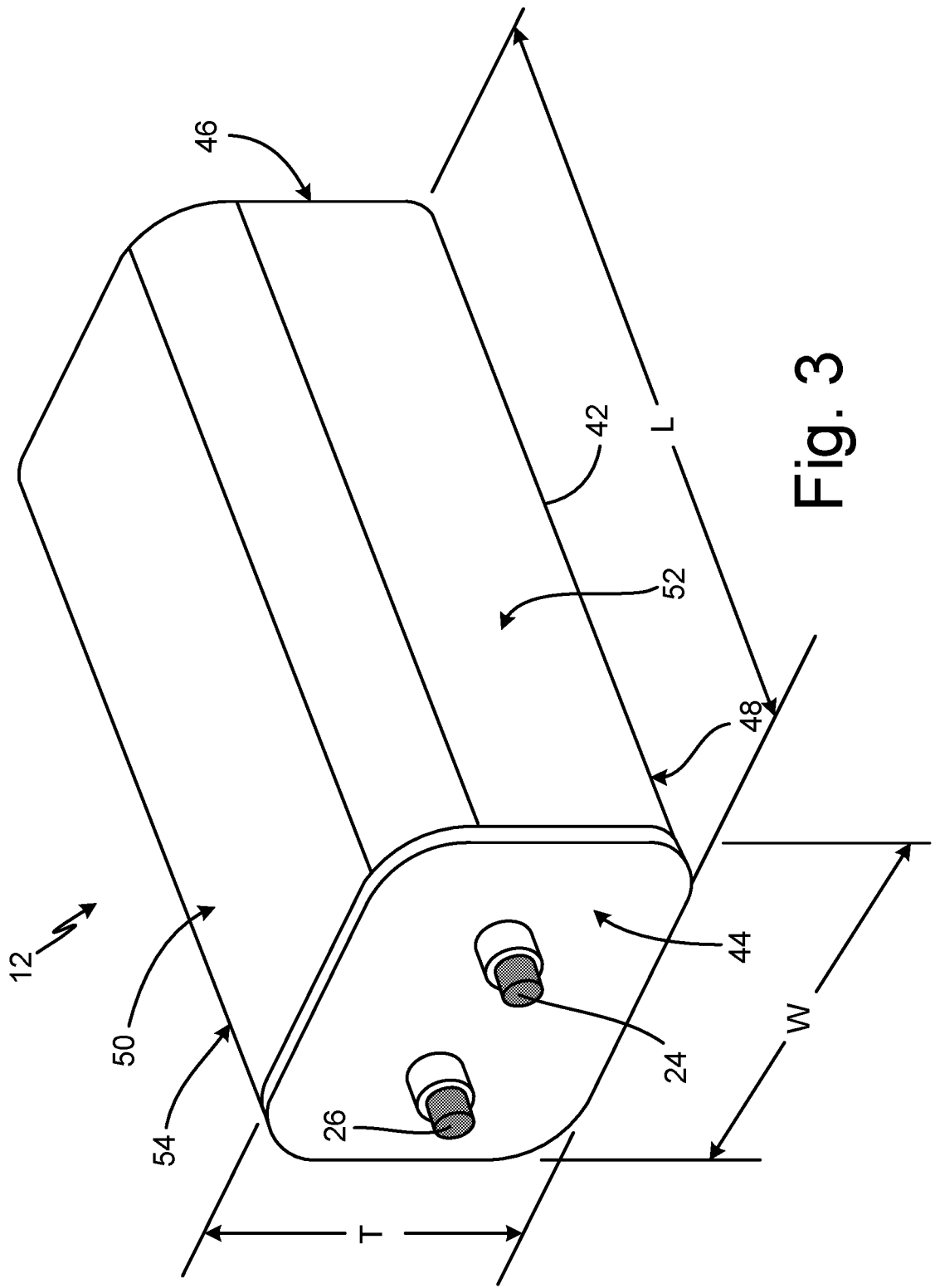
FIG. 3 is a perspective view of the portable air sensing device in an assembled state.

FIG. 3 is a perspective view of portable air sensing device 12 in an assembled state. As illustrated in FIG. 3, portable air sensing device 12 includes power button 24, wireless communications synchronization button 26, and outer housing 42. Outer housing 42 encloses the inner electronics of portable air sensing device 12 and can be formed of metal, plastic, or other rigid material that can enclose the inner electronics to provide structure to portable air sensing device 12 and protection to internal components of portable air sensing device 12 during transport and operation. Though outer housing 42 encloses the internal electrical components of portable air sensing device 12 (including the $CO_2$ sensor), outer housing 42 is not hermetically sealed, thereby allowing the $CO_2$ sensor enclosed by outer housing 42 to sense $CO_2$ concentrations of the surrounding air. In some examples, outer housing 42 can include ventilation holes or other passages to enable the $CO_2$ sensor to sense concentrations of $CO_2$ in the surrounding air.

As illustrated in FIG. 3, outer housing 42 of portable air sensing device 12 is generally rectangular in shape and has first end 44, second end 46, bottom 48, top 50, first side 52, and second side 54. Power button 24 and wireless communications synchronization button 26 are disposed at first end 44. Second end 46 is opposite and parallel to first end 44. Bottom 48 extends between and is orthogonal to both first and 44 and second end 46. Top 50 is parallel to bottom 48 and extends between first end 44 and second end 46. First side 52 is orthogonal to and extends between first end 44, second end 46, bottom 48, and top 50. Second side 54 is opposite and parallel to first side 52, and extends between first end 44, second end 46, bottom 48, and top 50.

Outer housing 42, as illustrated in FIG. 3, has length L between first end 44 and second end 46, thickness T between bottom 48 and top 50, and width W between first side 52 and second side 54. As previously described, air sensing device 12 is portable in nature, meaning that outer housing 42 has dimensions L, W, and T that enable air sensing device 12 to be transported with a pilot, copilot, or other flight crew between aircraft. For instance, in one example, outer housing 42 has length L that is approximately 5 inches (e.g., between 4.5 and 5.5 inches), width W that is approximately 3.5 inches (e.g., between 3 and 4 inches), and thickness T that is approximately 2.25 inches (e.g., between 2 and 2.5 inches). It should be appreciated that other dimensions L, W, and T of outer housing 42 are possible, but that air sensing device 12 is generally portable in nature, meaning that air sensing device 12 is small enough to enable transport of portable air sensing device 12 in, e.g., a pants pocket, a shirt pocket, and/or flight bag of the flight crew.

Figure 4:
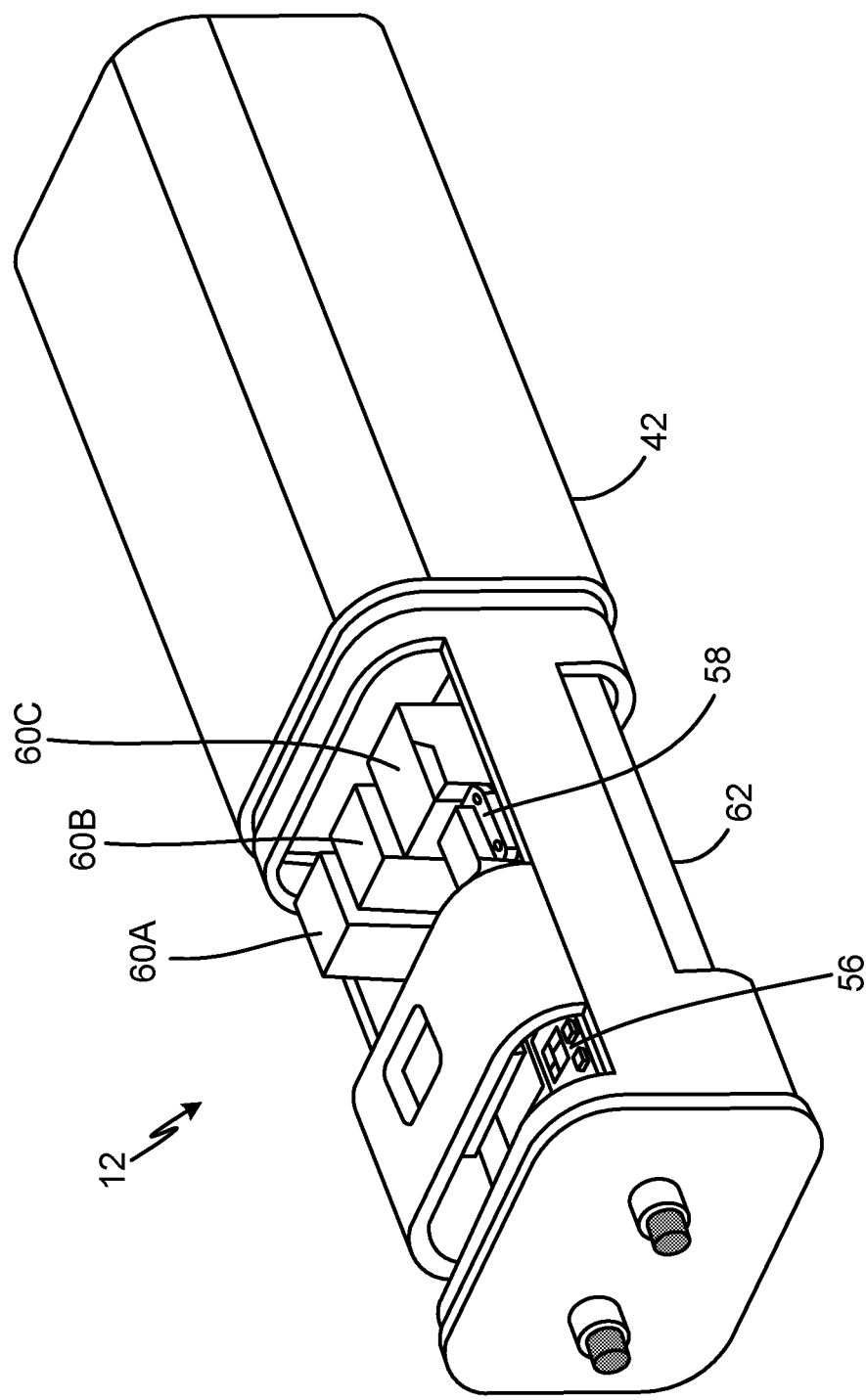
FIG. 4 is a perspective view of the portable air sensing device in a disassembled state and having a portion of the outer housing removed to illustrate internal electrical components.

FIG. 4 is a perspective view of portable air sensing device 12 in a disassembled state and having a portion of outer housing 42 removed to illustrate internal electrical components. That is, in the example of FIG. 4, a portion of outer housing 42 is removed to show processor 56, $CO_2$ sensor 58, interface ports 60A, 60B, and 60C, and battery 62 that are enclosed within outer housing 42 during an assembled state. The portion of outer housing 42 that is removed in the example of FIG. 4 can, in certain examples, be slidingly engaged and disengaged with the remainder of outer housing 42 to enable access to internal components (e.g., battery 62) of portable air sensing device 12. While illustrated in FIG. 4 as including $CO_2$ sensor 58, in some examples, portable air sensing device 12 can alternatively and/or additionally include component gas sensors configured to sense a concentration of a component gas other than $CO_2$, such as CO, TCP, VOCs, $O_3$, or other component gases.

Processor 56 is configured to implement functionality and/or process instructions within portable air sensing device 12. For instance, processor 56 can be capable of processing instructions stored at computer-readable memory of portable air sensing device 12, such as computer-readable memory mounted on a circuit board of processor 56. Examples of processor 56 can include any one or more of a microprocessor, a controller, a digital signal process (DSP), an application specific integrated circuit (ASIC), a field-programmable gate array (FPGA), or other equivalent discrete or integrated logic circuitry. In the example of FIG. 4, processor 56 is a Raspberry Pi processor having an integrated central processing unit (CPU), one or more communications units (e.g., WiFi and/or Bluetooth transceivers), on-board computer-readable memory, and interface ports 60A-60C that are usable to interface with components of processor 56.

Computer-readable memory of portable air sensing device 12 can be configured to store information within portable air sensing device 12 during operation. Computer-readable memory, in some examples, is described as a computer-readable storage medium. In some examples, a computer-readable storage medium can include a non-transitory medium. The term "non-transitory can indicate that the storage medium is not embodied in a carrier wave or a propagated signal. In certain examples, a non-transitory storage medium can store data that can, over time, change (e.g., in RAM or cache). Computer-readable memory of portable air sensing device 12 can include volatile and non-volatile storage elements. Examples of volatile memory include random access memory (RAM), dynamic random access memory (DRAM), static random access memory (SRAM), and other forms of volatile memory. Examples of non-volatile memory include magnetic hard discs, optical discs, floppy discs, flash memories, or other forms of electrically programmable memories (EPROM) or electrically erasable and programmable (EEPROM) memories.

Battery 62 is a Lithium-ion (Li-ion) or other type of battery configured to store and supply electrical power to components of portable air sensing device 12 during operation. In certain examples, battery 62 is a rechargeable battery that can be charged, discharged during operation of portable air sensing device 12, and recharged multiple times. $CO_2$ sensor 58 is a non-dispersive infrared (NDIR) sensor, a chemical $CO_2$ sensor, or other type of sensor capable of sensing a concentration of $CO_2$ in air. In the example of FIG. 4, $CO_2$ sensor 58 is a NDIR sensor having an effective measurement range from zero ppm to 10,000 ppm of $CO_2$ in air.

In operation, $CO_2$ sensor 58 senses a concentration of $CO_2$ in surrounding air at a measurement rate, such as once per second, once every two seconds, or other measurement rates. Processor 56 causes the sensed $CO_2$ concentration data to be transmitted (e.g., via analog signal, digital signal, or both) via a wireless communications device, such as a Bluetooth transceiver, a WiFi transceiver, or other wireless communications device integrated with or electrically and/or communicatively coupled with processor 56. In some examples, processor 56 transmits time data indicating a time at which the $CO_2$ concentration data was sensed. For instance, in some examples, processor 56 causes the $CO_2$ concentration data to be transmitted as IP packets including a time (and, in certain examples, a date) indicating when the data was transmitted, sensed, or both.

Accordingly, portable air sensing device 12 senses and wirelessly transmits concentration data of $CO_2$ for use by an EFB or other aircraft system to notify aircraft flight personnel (e.g., pilot, copilot, or other flight crew) of the concentration of $CO_2$ in the air of the cockpit. Such $CO_2$ concentration data can be displayed and/or utilized for generation of alerts when $CO_2$ concentrations are determined to meet or exceed defined threshold criteria.

Figure 5:
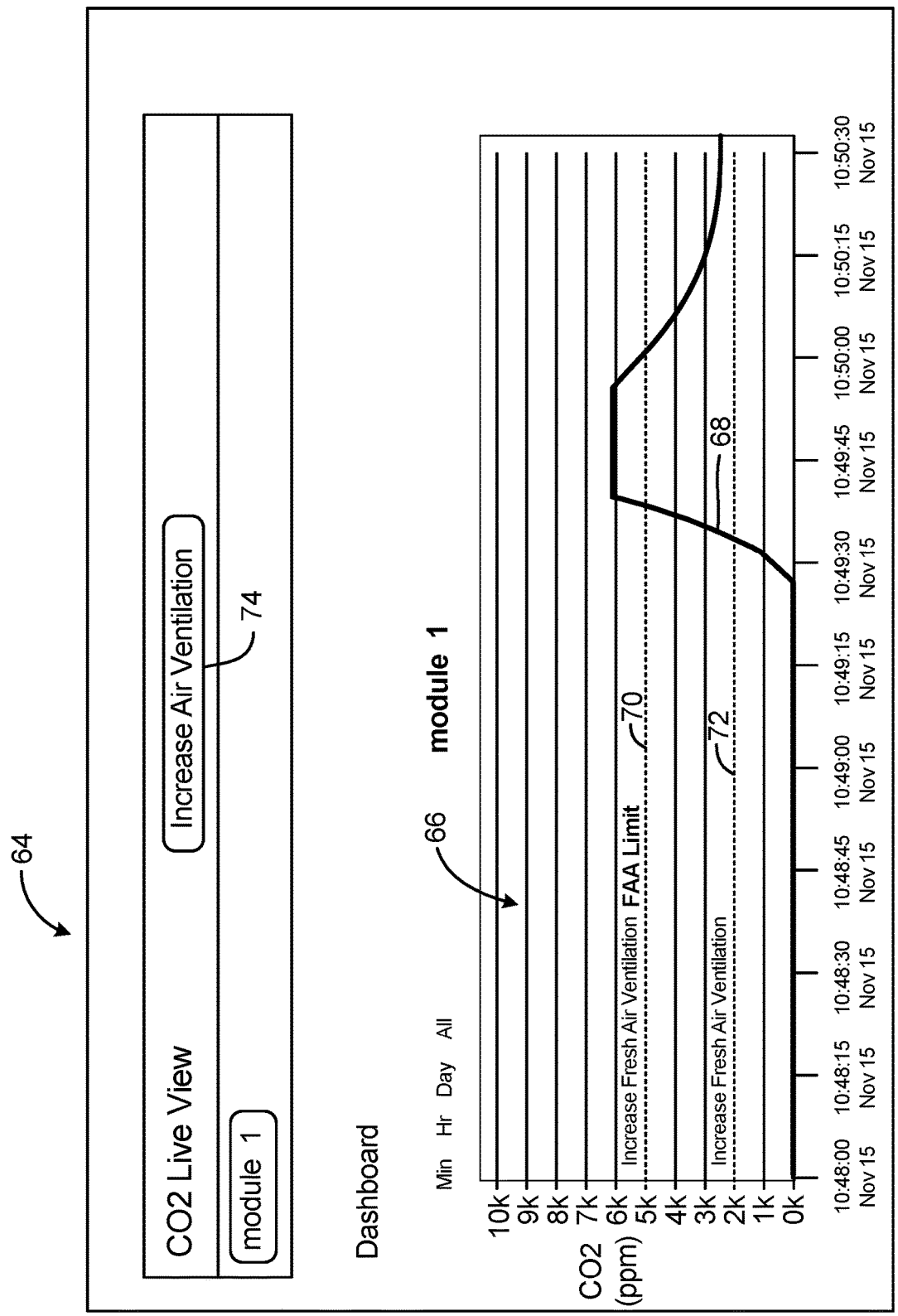
FIG. 5 is a screenshot of a carbon dioxide level display view showing a trend of measured carbon dioxide concentration over time.

FIG. 5 is a screenshot of $CO_2$ level display view 64 showing a graph of a sensed $CO_2$ concentration over time. $CO_2$ level display view 64 illustrates an example of display data generated by TIM 14 (FIG. 1), TIM 30A (FIG. 2) and/or TIM 30B (FIG. 2) indicating the sensed $CO_2$ concentration data received from portable air sensing device 12 (FIGS. 1-4). As illustrated in FIG. 5, $CO_2$ level display view 64 includes $CO_2$ concentration trend plot 66 showing a series of $CO_2$ concentrations (on the vertical axis) with respect to time (on the horizontal axis) as $CO_2$ trend line 68. In addition, $CO_2$ concentration trend plot 66 shows first maximum threshold $CO_2$ concentration line 72 at 2000 ppm of $CO_2$ and second maximum threshold $CO_2$ concentration line 70 at 5000 ppm of $CO_2$. First maximum threshold $CO_2$ concentration line 72 (e.g., at 2000 ppm in the example of FIG. 5) corresponds to a first defined maximum threshold $CO_2$ concentration, above which human cognitive abilities may begin to diminish. Second maximum threshold $CO_2$ concentration line 70 (e.g., at 5000 ppm in the example of FIG. 5) corresponds to a second defined maximum threshold $CO_2$ concentration, above which human cognitive abilities are known to diminish and corresponding to an advisory limit established by the United States Federal Aviation Administration (FAA).

In the example of FIG. 5, sensed $CO_2$ concentrations received from portable air sensing device 12 exceeded 5000 ppm to a maximum of approximately 6000 ppm and subsequently reduced to an amount that is less than 5000 ppm but greater than 2000 ppm (e.g., approximately 2500 ppm). Alert 74 is generated and displayed in response to determining that the sensed $CO_2$ concentration levels received from portable air sensing device 12 exceeds one or more of the $CO_2$ concentrations associated with first maximum threshold $CO_2$ concentration line 72 and second maximum threshold $CO_2$ concentration line 70. In the example of FIG. 5, alert 74 includes a recommendation of remedial action to increase air ventilation, such as by activating an ECS of the aircraft. While the example of FIG. 5 is described above with respect to $CO_2$ concentrations, it should be understood that the example techniques are also applicable to concentrations of other component gases, such as CO, TCP, VOCs, $O_3$, or other component gases.

Accordingly, portable air sensing device 12 senses $CO_2$ concentration of cockpit air and wirelessly transmits the $CO_2$ concentration data to an electronic interface device, such as a Tablet Interface Device of an aircraft EFB system for display, trend plotting, and alert generation when $CO_2$ concentration levels are elevated. As such, systems implementing techniques described herein can alert pilots, copilots, and other flight crew of elevated $CO_2$ concentrations to enable corrective action to help prevent exposure to $CO_2$ concentration levels that can diminish human cognitive abilities.

DISCUSSION OF POSSIBLE EMBODIMENTS

The following are non-exclusive descriptions of possible embodiments of the present invention.

A system includes a portable air sensing device and an electronic interface device. The portable air sensing device is configured to sense a concentration of a component gas in surrounding air and wirelessly transmit the sensed concentration. The electronic interface device is positioned within a cockpit of an aircraft and is communicatively coupled with the portable air sensing device. The electronic interface device is configured to receive the wirelessly transmitted concentration from the portable air sensing device, and generate, for display, an indication of the received concentration in relation to a defined threshold maximum concentration of the component gas.

The system of the preceding paragraph can optionally include, additionally and/or alternatively, any one or more of the following features, configurations and/or additional components:

The component gas can include carbon dioxide gas.

The component gas can include at least one of carbon monoxide, tricresyl phosphate (TCP), a volatile organic compound (VOC), and ozone.

The electronic interface device can be further configured to generate an alert in response to determining that the received concentration exceeds the defined threshold maximum concentration of the component gas.

The alert can include a recommended remedial action.

The recommended remedial action can include activation an environmental control system of the aircraft.

The portable air sensing device can be further configured to wirelessly transmit time data identifying a time when the concentration of the component gas was sensed.

The electronic interface device can be further configured to receive the wirelessly transmitted time data from the portable air sensing device. The electronic interface device can be configured to generate, for display, the indication of the received concentration of the component gas in relation to the defined threshold maximum concentration of the component gas as a time series of concentrations in relation to the defined threshold maximum concentration of the component gas.

The electronic interface device can be a tablet interface module of an electronic flight bag (EFB) system configured to display aircraft operating manual information, flight crew operating manual information, and navigational charts.

The system can further include a display device communicatively coupled with the electronic interface device and configured to receive and display the indication of the concentration of the component gas in relation to the defined threshold maximum concentration of the component gas.

The display device can be a portable computing device.

The display device can be communicatively coupled with the electronic interface device to receive the indication of the concentration of the component gas in relation to the defined threshold maximum concentration of the component gas via wireless communications.

The electronic interface device can be configured to generate the indication of the received concentration data in relation to the defined threshold maximum concentration of the component gas as a Hypertext Transfer Protocol (HTTP) based web page.

The portable air sensing device can further include a battery configured to supply electrical power for operation of the portable air sensing device.

A system includes a portable air sensing device, an electronic interface device, and a portable computing device having a display. The portable air sensing device is configured to sense a concentration of a component gas in surrounding air and wirelessly transmit the sensed concentration and time data identifying a time when the concentration of the component gas was sensed. The electronic interface device is positioned within a cockpit of an aircraft and is communicatively coupled with the portable air sensing device. The electronic interface device is configured to receive the wirelessly transmitted concentration of the component gas and time data from the portable air sensing device, and generate, for display, an indication of the received concentration of the component gas in relation to the time data. The portable computing device is communicatively coupled to the electronic interface device and is configured to display the indication of the received concentration of the component gas in relation to the time data.

The system of the preceding paragraph can optionally include, additionally and/or alternatively, any one or more of the following features, configurations and/or additional components:

The portable computing device can be a portable tablet computer.

The electronic interface device can be configured to generate the indication of the received concentration of the component gas in relation to the time data via a web page.

The portable tablet computer can be configured to execute a web browser application to access the web page via Hypertext Transfer Protocol (HTTP) communications.

The component gas can include at least one of carbon dioxide, carbon monoxide, tricresyl phosphate (TCP), a volatile organic compound (VOC), and ozone.

A method includes sensing, by a gas sensor of a portable air sensing device, concentration of a component gas in surrounding air, and wirelessly transmitting, by the portable air sensing device, the sensed concentration of the component gas. The method further includes receiving, by an electronic interface device positioned within a cockpit of an aircraft, the sensed concentration of the component gas wirelessly transmitted by the portable air sensing device, and generating, by the electronic interface device, an indication of the received concentration of the component gas for display in relation to a defined threshold maximum concentration of the component gas.

The method can further include generating, by the electronic interface device, an alert in response to determining that the received concentration of the component gas exceeds the defined maximum concentration of the component gas.

The method can further include: wirelessly transmitting, by the portable air sensing device, time data identifying a time when the concentration of the component gas was sensed; and receiving, by the electronic interface device, the wirelessly transmitted time data from the portable air sensing device. Generating the indication of the received concentration of the component gas for display can include generating the indication of the received concentration of the component gas in relation to the defined threshold maximum concentration of the component gas as a time series of concentrations in relation to the defined threshold maximum concentration presented in a Hypertext Transfer Protocol (HTTP) based web page.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system comprising:
a portable air sensing device configured to sense a concentration of a component gas in surrounding air and wirelessly transmit the sensed concentration; and
an electronic interface device positioned within a cockpit of an aircraft and communicatively coupled with the portable air sensing device, the electronic interface device configured to:
receive the wirelessly transmitted concentration from the portable air sensing device;
generate, for display, an indication of the received concentration in relation to a defined threshold maximum concentration of the component gas; and
generate an alert in response to determining that the received concentration exceeds the defined threshold maximum concentration of the component gas;
wherein the alert comprises a recommended remedial action; and
wherein the recommended remedial action comprises activation of an environmental control system of the aircraft.

2. The system of claim 1,
wherein the component gas comprises carbon dioxide gas.

3. The system of claim 1,
wherein the component gas comprises at least one of carbon monoxide, tricresyl phosphate (TCP), a volatile organic compound (VOC), and ozone.

4. The system of claim 1,
wherein the electronic interface device is a tablet interface module of an electronic flight bag (EFB) system configured to display aircraft operating manual information, flight crew operating manual information, and navigational charts.

5. The system of claim 1,
wherein the electronic interface device is configured to generate the indication of the received concentration data in relation to the defined threshold maximum concentration of the component gas as a Hypertext Transfer Protocol (HTTP) based web page.

6. The system of claim 1,
wherein the portable air sensing device is further configured to wirelessly transmit time data identifying a time when the concentration of the component gas was sensed.

7. The system of claim 6,
wherein the electronic interface device is further configured to receive the wirelessly transmitted time data from the portable air sensing device; and
wherein the electronic interface device is configured to generate, for display, the indication of the received concentration of the component gas in relation to the defined threshold maximum concentration of the component gas as a time series of concentrations in relation to the defined threshold maximum concentration of the component gas.

8. The system of claim 1, further comprising:
a display device communicatively coupled with the electronic interface device and configured to receive and display the indication of the concentration of the component gas in relation to the defined threshold maximum concentration of the component gas.

9. The system of claim 8,
wherein the display device is a portable computing device.

10. The system of claim 8,
wherein the display device is communicatively coupled with the electronic interface device to receive the indication of the concentration of the component gas in relation to the defined threshold maximum concentration of the component gas via wireless communications.

11. A system comprising:
a portable air sensing device configured to sense a concentration of a component gas in surrounding air and wirelessly transmit the sensed concentration and time data identifying a time when the concentration of the component gas was sensed;
an electronic interface device positioned within a cockpit of an aircraft and communicatively coupled with the portable air sensing device, the electrical interface device configured to:
receive the wirelessly transmitted concentration of the component gas and time data from the portable air sensing device;

generate, for display, an indication of the received concentration of the component gas in relation to the time data; and generate an alert in response to determining that the received concentration exceeds the defined threshold maximum concentration of the component gas;

wherein the alert comprises a recommended remedial action; and wherein the recommended remedial action comprises activation of an environmental control system of the aircraft; and a portable computing device having a display, the portable computing device communicatively coupled to the electronic interface device and configured to display the indication of the received concentration of the component gas in relation to the time data.

12. The system of claim 11, wherein the component gas comprises at least one of carbon dioxide, carbon monoxide, tricresyl phosphate (TCP), a volatile organic compound (VOC), and ozone.

13. The system of claim 11, wherein the portable computing device comprises a portable tablet computer.

14. The system of claim 13,
wherein the electronic interface device is configured to generate the indication of the received concentration of the component gas in relation to the time data via a web page; and wherein the portable tablet computer is configured to execute a web browser application to access the web page via Hypertext Transfer Protocol (HTTP) communications.

15. A method comprising:
sensing, by a gas sensor of a portable air sensing device, concentration of a component gas in surrounding air;

wirelessly transmitting, by the portable air sensing device, the sensed concentration of the component gas;

receiving, by an electronic interface device positioned within a cockpit of an aircraft, the sensed concentration of the component gas wirelessly transmitted by the portable air sensing device;

generating, by the electronic interface device, an indication of the received concentration of the component gas for display in relation to a defined threshold maximum concentration of the component gas; and generating, by the electronic interface device, an alert in response to determining that the received concentration of the component gas exceeds the defined maximum concentration of the component gas;

wherein the alert comprises a recommended remedial action; and wherein the recommended remedial action comprises activation of an environmental control system of the aircraft.

16. The method of claim 15, further comprising:
wirelessly transmitting, by the portable air sensing device, time data identifying a time when the concentration of the component gas was sensed; and receiving, by the electronic interface device, the wirelessly transmitted time data from the portable air sensing device;

wherein generating the indication of the received concentration of the component gas for display comprises generating the indication of the received concentration of the component gas in relation to the defined threshold maximum concentration of the component gas as a time series of concentrations in relation to the defined threshold maximum concentration presented in a Hypertext Transfer Protocol (HTTP) based web page.

* * * * *